(12) United States Patent
Sawada et al.

(10) Patent No.: US 11,215,995 B2
(45) Date of Patent: Jan. 4, 2022

(54) ENVIRONMENT IMPROVEMENT SYSTEM AND ENVIRONMENT IMPROVEMENT METHOD, AND SERVER USED THEREIN

(71) Applicant: TOYOTA JIDOSHA KABUSHIKI KAISHA, Toyota (JP)

(72) Inventors: Hiroki Sawada, Toyota (JP); Masato Tamaoki, Iwakura (JP); Eisuke Ando, Nagoya (JP); Masato Endo, Nagakute (JP); Kuniaki Hasegawa, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 27 days.

(21) Appl. No.: 16/184,935

(22) Filed: Nov. 8, 2018

(65) Prior Publication Data

US 2019/0146506 A1 May 16, 2019

(30) Foreign Application Priority Data

Nov. 13, 2017 (JP) .............................. JP2017-218407

(51) Int. Cl.
*G05D 1/02* (2020.01)
*H04W 4/40* (2018.01)
*G01N 33/00* (2006.01)

(52) U.S. Cl.
CPC ........ *G05D 1/0212* (2013.01); *G01N 33/0073* (2013.01); *G05D 1/0287* (2013.01); *H04W 4/40* (2018.02)

(58) Field of Classification Search
CPC ..... G05D 1/0212; G05D 1/0287; H04W 4/40; H04W 4/38; H04W 4/025; G01N 33/0073
See application file for complete search history.

(56) References Cited

U.S. PATENT DOCUMENTS 5,147,429 A * 9/1992 Bartholomew ........ B01D 46/42
244/30
9,375,847 B2 * 6/2016 Angle .................. G05D 1/0022
(Continued)

FOREIGN PATENT DOCUMENTS

EP 2945783 A1 * 11/2015 ........... G05D 1/0016
EP 2945783 B1 * 10/2019 ........... A47L 9/2857
(Continued)

OTHER PUBLICATIONS

English translation of Kim, 2008.*
(Continued)

*Primary Examiner* — Donald J Wallace
*Assistant Examiner* — Daniel M. Robert
(74) *Attorney, Agent, or Firm* — Hunton Andrews Kurth LLP

(57) ABSTRACT

An environment improvement system includes: a sensor configured to detect a state of pollution by an environmental pollutant; a plurality of vehicles; and a server configured to communicate with the plurality of vehicles. The plurality of vehicles include vehicles including environment improvement devices configured to remove the environmental pollutant. When a pollution level by the environmental pollutant exceeds a threshold value in an area where the sensor is located, the server is configured to select at least a part of the vehicles including the environment improvement devices and cause the selected vehicles to move to the area, and to output a command to execute an environment improvement operation using the environment improvement devices.

11 Claims, 7 Drawing Sheets

(56) References Cited

U.S. PATENT DOCUMENTS

| | | | | |
|---|---|---|---|---|
| 10,089,586 | B2* | 10/2018 | Vestal | G16H 40/20 |
| 2004/0093264 | A1* | 5/2004 | Shimizu | G07C 5/008 |
| | | | | 705/13 |
| 2008/0098562 | A1* | 5/2008 | Tagliaferri | E01H 1/00 |
| | | | | 15/340.1 |
| 2014/0379127 | A1 | 12/2014 | Tsuboi et al. | |
| 2016/0135655 | A1* | 5/2016 | Ahn | G05D 1/0044 |
| | | | | 134/56 R |

FOREIGN PATENT DOCUMENTS

| | | | | | |
|---|---|---|---|---|---|
| JP | 2001-319291 | A | | 11/2001 | |
| JP | 2004-157842 | A | | 6/2004 | |
| JP | 2013146310 | A | * | 8/2013 | A47L 9/2868 |
| JP | 2013146310 | A | | 8/2013 | |
| JP | 2017044408 | A | | 3/2017 | |
| KR | 100631536 | B1 | * | 10/2006 | B01D 46/46 |
| KR | 100791382 | B1 | * | 1/2008 | B25J 19/023 |

OTHER PUBLICATIONS

Ferri et al. "Dustcart, a Mobile Robot for Urban Environments: Experiments of Pollution Monitoring and Mapping during Autonomous Navigation in Urban Scenarios," in Proceedings of International Conference on Robotics and Automation (ICRA 2010) Workshop on Networked and Mobile Robot . . . (Year: 2010).*

Mazzolai et al., "The Dustcart service robt at work in the town of Peccioli: focus on social and legal challenges," ICAR 2011 Workshop, http://www.icar2011.org/files/Mazzolai_ICAR2011-WS%20Urban%20Robotics.pdf (Year: 2011).*

Gabriele Ferri et al. (Gabriele Ferri; Alessio Mondini; Alessandro Manzi; Barbara Mazzolai; Cecilia Laschi; Virgilio Mattoli; Matteo Reggente; Todor Stoyanov; Achim J. Lilienthal; Marco Lettere; Paolo Dario (May 2010), "DustCart, a Mobile Robot for Urban Environments" (Year: 2010).*

Ref V. Continued in Proceedings of International Conference on Robotics and Automation (ICRA 2010) Workshop on Networked and Mobile Robot Olfaction in Natural, Dynamic Environments. (Year: 2010).*

Ref V further continued: http://130.243.105.49/Research/mro/publications/2010/Ferri_etal_2010-ICRA_WS10-DustCart_Mobile_Robot_Urban_Environments_Experiments_Pollution_Monitoring_Mapping_Urban_Scenarios.pdf (Year: 2010).*

* cited by examiner

FIG.3

| VEHICLE ID | DATE | VEHICLE POSITION | DETECTED CONCENTRATION (ppm) | AVAILABLE TIME PERIOD | POSSIBILITY OF MOVEMENT |
|---|---|---|---|---|---|
| A1234 | 2017/10/20 10:10:20 | (X1, Y1, Z1) | 10 | 10:00-14:00 | POSSIBLE |
| A2345 | 2017/10/20 10:05:30 | (X2, Y2, Z2) | 20 | 17:00-24:00 | IMPOSSIBLE |
| B3456 | 2017/10/20 10:00:40 | (X3, Y3, Z3) | 100 | 08:00-15:00 | POSSIBLE |
| C4567 | 2017/10/20 10:12:35 | (X4, Y4, Z4) | 5 | 12:00-15:00 | POSSIBLE |
| D5678 | 2017/10/20 10:09:00 | (X5, Y5, Z5) | 60 | 06:00-10:00 | POSSIBLE |

FIG.5

| AREA | POLLUTION LEVEL (ppm) | NECESSITY OF IMPROVEMENT | SELECTED VEHICLE ID |
|---|---|---|---|
| A | 10 | UNNECESSARY | |
| B | 300 | NECESSARY | A1234, D5123, F8546, G5564 |
| C | 20 | UNNECESSARY | |
| D | 180 | NECESSARY | B2344, C8542, E4621 |
| E | 200 | NECESSARY | A6582, M4522, F1223 |
| F | 50 | UNNECESSARY | |
| G | 150 | NECESSARY | C1597, D5547, H2541 |
| H | 30 | UNNECESSARY | |

FIG.6

| VEHICLE ID | AREA | MOVEMENT POSITION | OPERATION MANNER |
|---|---|---|---|
| A1234 | A | (X6, Y6, Z6) | STOP |
| D5123 | A | (X7, Y7, Z7) | TRAVEL |
| F8546 | A | (X8, Y8, Z8) | TRAVEL |
| G5564 | A | (X9, Y9, Z9) | TRAVEL |
| B2344 | D | (X10, Y10, Z10) | STOP |
| C8542 | D | (X11, Y11, Z11) | TRAVEL |
| C1597 | G | (X16, Y16, Z16) | TRAVEL |
| D5547 | G | (X17, Y17, Z17) | TRAVEL |
| H2541 | G | (X18, Y18, Z18) | TRAVEL |

ENVIRONMENT IMPROVEMENT SYSTEM AND ENVIRONMENT IMPROVEMENT METHOD, AND SERVER USED THEREIN

This nonprovisional application is based on Japanese Patent Application No. 2017-218407 filed on Nov. 13, 2017 with the Japan Patent Office, the entire contents of which are hereby incorporated by reference.

BACKGROUND

Field

The present disclosure relates to an environment improvement system and an environment improvement method, and a server used therein. More particularly, the present disclosure relates to the technique of improving the environment by using an environment improvement device mounted on a movable body.

Description of the Background Art

There are concerns about an influence of a particulate matter such as pollen, yellow sand, dust, or soot generated by combustion on human health. Particularly, a fine particulate matter having a particle size of not more than approximately 2.5 µm (so-called PM2.5) easily enters an alveolus in a human body because the particle size is very small. The relevance between such a particulate matter and a respiratory system disease or circulatory system disease is under study.

On the other hand, a method for reducing such an environmental pollutant has been proposed. For example, Japanese Patent Laying-Open No. 2001-319291 discloses the technique of controlling a traffic light based on a concentration of an environmental pollution gas detected by a gas sensor placed on a road and suppressing an amount of vehicles entering a region having a high concentration of the environmental pollution gas, to thereby reduce the concentration of the environmental pollution gas in the region.

In addition, Japanese Patent Laying-Open No. 2004-157842 discloses the technique of calculating an amount of release of an air pollutant in a control center, based on information transmitted from a sensor attached to each vehicle, and providing diagnosis result and advice for encouraging a driver of the vehicle to perform ecological driving, based on the information.

SUMMARY

An object of the techniques disclosed in the above-described patent literatures is to reduce the air pollutant (environmental pollutant) released from the vehicle. However, improving the environment by removing the already-generated air pollutant is not discussed.

On the other hand, an air cleaner configured to remove pollen, PM2.5 and the like has been developed, and a vehicle having such an environment improvement device mounted thereon is increasing. By using such an environment improvement device mounted on the vehicle, a state of environmental pollution may be improved.

The present disclosure has been made to solve the above-described problem, and an object of the present disclosure is to provide an environment improvement system configured to improve a state of environmental pollution by using a movable body having an environment improvement device mounted thereon.

An environment improvement system according to the present disclosure includes: a sensor configured to detect a state of pollution by an environmental pollutant; a plurality of movable bodies; and a server configured to communicate with the plurality of movable bodies. The plurality of movable bodies include movable bodies including environment improvement devices configured to remove the environmental pollutant. When the state of pollution detected by the sensor enters a state in which removal of the environmental pollutant is necessary in an area where the sensor is located, the server is configured to (i) select at least a part of the movable bodies including the environment improvement devices and cause the selected movable bodies to move to the area, and (ii) output a command to execute an environment improvement operation using the environment improvement devices.

According to the present disclosure, the server determines an area having a high pollution level by the environmental pollutant, and dispatches the movable bodies (e.g., vehicles) having the environment improvement devices mounted thereon to the area and causes the dispatched movable bodies to execute the environment improvement operation. As a result, the environmental pollutant in the area can be removed and the pollution level can be reduced, and thus, a state of environmental pollution can be improved.

The plurality of movable bodies include a movable body including the sensor.

When the pollution level is determined based only on information from a fixed sensor, environment improvement in the entire area may be impossible if the state of pollution in the area is not uniform. By using the sensor mounted on the movable body, the state of pollution can be detected in a wider range in the area. Thus, the state of environmental pollution can be appropriately improved in the entire area.

The server is configured to calculate a pollution level for each predetermined area, using position information of the movable body including the sensor and information about the state of pollution, and determine necessity of removal of the environmental pollutant, using the pollution level.

With such a configuration, the position information of the moving movable body and the state of pollution can be associated with each other and the pollution level can be calculated, and thus, the state of environmental pollution in the area can be detected more appropriately.

The server is configured to select a movable body including an environment improvement device corresponding to a type of the environmental pollutant, of the movable bodies including the environment improvement devices.

Generally, a type of an environmental pollutant that can be removed by the environment improvement device is specified in many cases, and the effect of environment improvement cannot be expected for an environmental pollutant that is not a target of removal. Therefore, by selecting the movable body including the environment improvement device corresponding to the type of the generated environmental pollutant when executing the environment improvement operation, the environment can be reliably improved.

The movable bodies including the environment improvement devices are configured such that an available time period thereof can be preset by a user. The server is configured to cause each selected movable body to execute the environment improvement operation within the available time period.

When a privately-owned vehicle is used as the movable body used for the environment improvement operation, it is not preferable to interfere with the use by the user and use the vehicle for the environment improvement operation. By taking the available time period preset by the user into consideration when the server selects the movable bodies, it is possible to contribute to environment improvement while satisfying the user's needs.

At least a part of the selected movable bodies execute the environment improvement operation while moving in a specified area.

Since at least a part of the selected movable bodies move while operating the environment improvement devices as described above, the environmental pollutant can be removed over a wide range and non-uniformity of the state of environmental pollution in the area can be reduced.

A movable body including both the sensor and the environment improvement device, of the plurality of movable bodies, executes the environment improvement operation regardless of reception of the command from the server, when the state of pollution detected by the sensor provided in the movable body enters the state in which removal of the environmental pollutant is necessary.

The movable body including the sensor can easily determine that execution of the environment improvement operation is necessary at the current position of the movable body, when the state of pollution detected by the sensor enters the state in which removal of the environmental pollutant is necessary. Therefore, the movable body including not only the sensor but also the environment improvement device can determine by itself the necessity of execution of the environment improvement operation, and thus, can execute the environment improvement operation with good response.

A server according to another aspect of the present disclosure is used in a system configured to improve a state of pollution by an environmental pollutant by using movable bodies having environment improvement devices mounted thereon. The server is configured to communicate with a plurality of movable bodies. The plurality of movable bodies include the movable bodies having the environment improvement devices mounted thereon. The server is configured to: (a) obtain information about the state of pollution by the environmental pollutant from a sensor; (b) using the information from the sensor, determine whether or not the state of pollution in an area where the sensor is located is a state in which removal of the environmental pollutant is necessary; (c) when it is determined that removal of the environmental pollutant in the area is necessary, select at least a part of the movable bodies having the environment improvement devices mounted thereon; and (d) cause the selected movable bodies to move to the area and execute an environment improvement operation using the environment improvement devices in the area.

An environment improvement method according to still another aspect of the present disclosure is an environment improvement method for improving an environment of an area where a sensor is located by using environment improvement devices mounted on movable bodies in a system, based on a state of pollution by an environmental pollutant detected by the sensor, the system including a plurality of movable bodies and a server configured to communicate with the plurality of movable bodies. The plurality of movable bodies include the movable bodies having the environment improvement devices mounted thereon. The environment improvement method includes, by the server: (a) determining whether or not the state of pollution in the area is a state in which removal of the environmental pollutant is necessary; (b) when it is determined that removal of the environmental pollutant in the area is necessary, selecting at least a part of the movable bodies having the environment improvement devices mounted thereon; (c) causing the selected movable bodies to move to the area; and (d) causing the selected movable bodies to execute an environment improvement operation using the environment improvement devices in the area.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 3 shows one example of contents of vehicle information transmitted from the vehicle to the server.

FIG. 5 shows one example of determination of necessity of environment improvement, and vehicle selection that are executed by the server.

FIG. 6 shows one example of contents of a command provided from the server to the vehicle.

DESCRIPTION OF THE PREFERRED EMBODIMENTS

Figure 1:
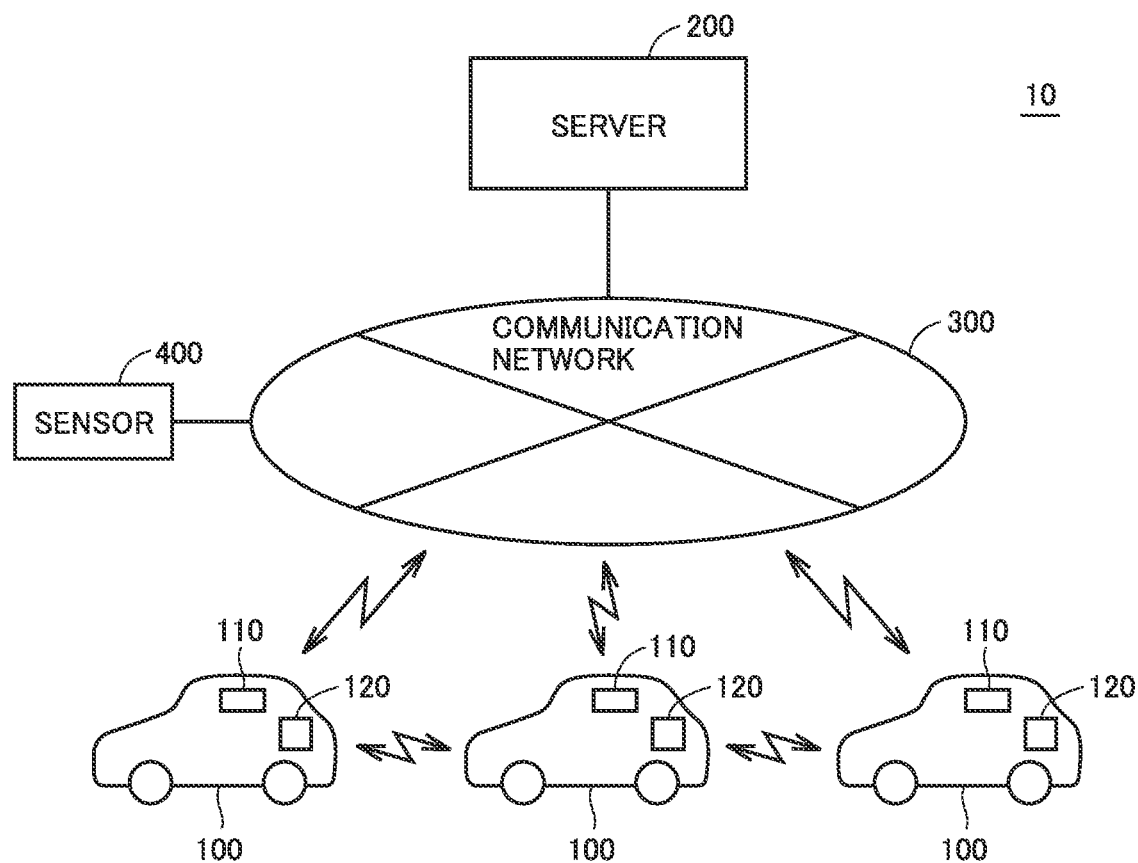
FIG. 1 is a schematic diagram of an overall configuration of an environment improvement system according to the present embodiment.

An embodiment of the present disclosure will be described in detail hereinafter with reference to the drawings, in which the same or corresponding portions are denoted by the same reference characters and description thereof will not be repeated.

(Overview of System)

FIG. 1 is a schematic diagram of an overall configuration of an environment improvement system 10 according to the present embodiment. Referring to FIG. 1, environment improvement system 10 includes a plurality of movable bodies 100, and a server 200 configured to communicate with movable bodies 100.

In the present embodiment, the case of using a vehicle as movable body 100 will be described, and movable body 100 will be also simply referred to as "vehicle 100" hereinafter. Vehicle 100 includes an automobile, a motorcycle, a bicycle and the like.

Vehicles 100 and server 200 are configured to mutually exchange information via a communication network 300 such as, for example, the Internet or a telephone line. Vehicles 100 and server 200 may directly communicate with each other without communication network 300. Direct communication between vehicles 100 is also possible.

Vehicle 100 is an electrically-powered vehicle that can travel using the electric power provided from a battery mounted thereon. Examples of the electrically-powered vehicle include an electric vehicle, a hybrid vehicle, a fuel cell vehicle and the like. A vehicle that travels using only the driving force generated in an internal combustion engine can also be used as vehicle 100. However, in the present embodiment, an electrically-powered vehicle with a relatively small amount of release of an air pollutant (hereinafter also referred to as "environmental pollutant") is preferably used from the perspective of environment improvement.

Vehicle 100 includes a sensor unit 110 configured to detect a concentration of a particulate matter such as pollen or PM2.5 or a gaseous air pollutant such as sulfur oxide (SOx) or nitrogen oxide (NOx). Vehicle 100 also includes an environment improvement device 120 such as an air cleaner or a bag filter configured to remove the air pollutant.

Server 200 obtains, through communication network 300, the concentration of the environmental pollutant detected by sensor unit 110 mounted on vehicle 100 or a sensor 400 fixed on the roadside or the like, and calculates a pollution level in a prescribed area. When the calculated pollution level becomes worse and exceeds a prescribed threshold value, server 200 causes vehicles 100 located in the area or in an area close thereto to move to within the area, and to operate environment improvement devices 120 mounted on vehicles 100. As a result, the environmental pollutant in the area having a high pollution level is removed and the environment is improved.

(Configuration of Vehicle and Server)

Figure 2:
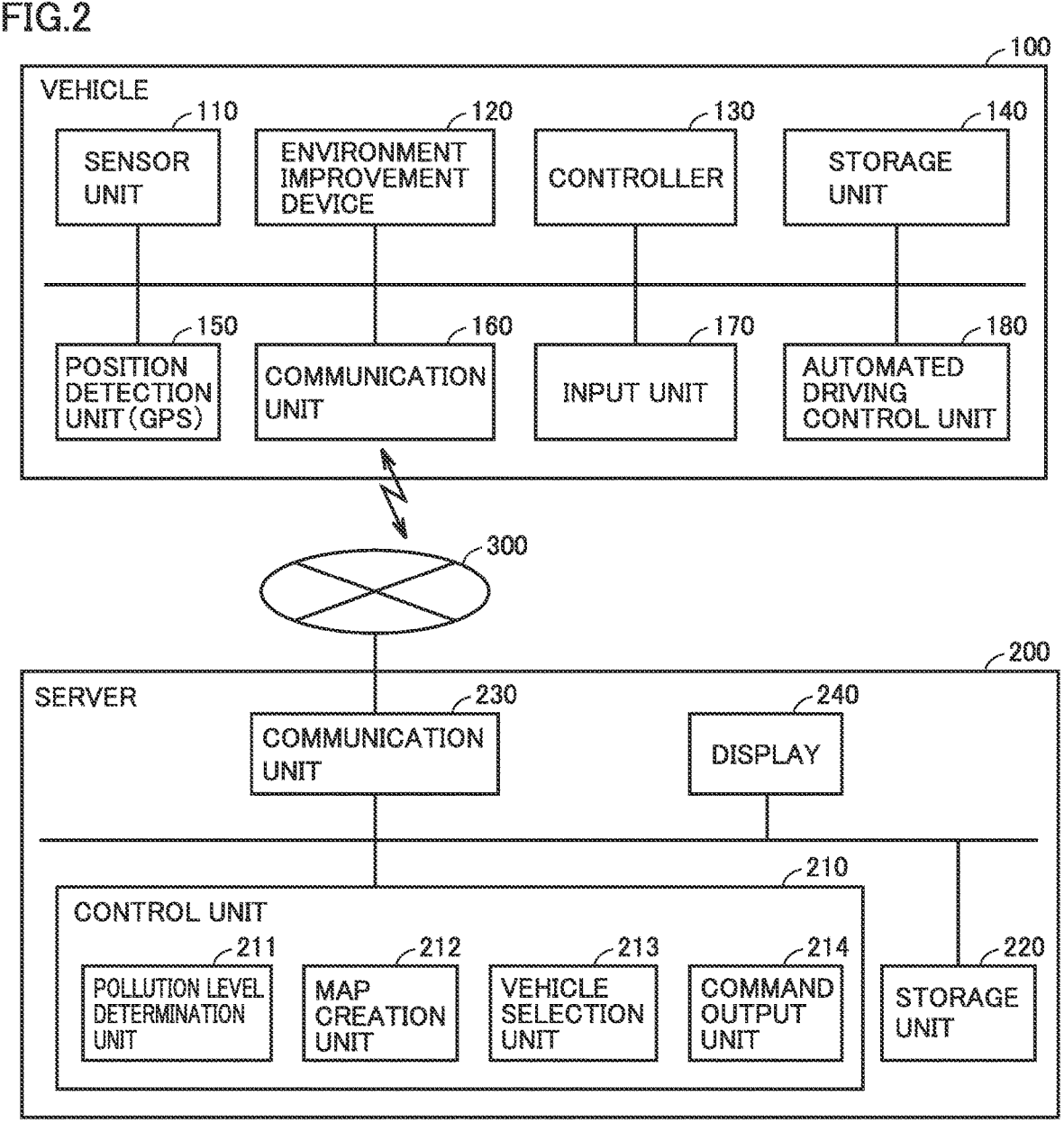
FIG. 2 is a block diagram for illustrating details of a vehicle and a server in FIG. 1.

FIG. 2 is a block diagram for illustrating details of vehicle 100 and server 200 in FIG. 1. Referring to FIG. 2, in addition to sensor unit 110 configured to detect the environmental pollutant and environment improvement device 120 configured to remove the environmental pollutant, vehicle 100 further includes a controller 130, a storage unit 140, a position detection unit 150, a communication unit 160, an input unit 170, and an automated driving control unit 180.

Communication unit 160 is a communication interface between vehicle 100 and communication network 300. Vehicle 100 performs wireless communication with communication network 300 via communication unit 160, and receives and transmits information to and from server 200. Vehicle 100 can also perform vehicle-to-vehicle communication with another vehicle via communication unit 160.

Although not shown, controller 130 includes a CPU (Central Processing Unit), a storage device such as a memory, and an input/output buffer, and provides comprehensive control of vehicle 100. Controller 130 receives a command from server 200 via communication unit 160. Upon receiving a command to move vehicle 100 from server 200, controller 130 causes automated driving control unit 180 to execute automated driving of vehicle 100, thereby moving vehicle 100 to a position specified by server 200. Controller 130 also controls start or stop of environment improvement device 120 based on a command from server 200.

Storage unit 140 is configured to include a recording device such as, for example, a nonvolatile memory or an HDD (Hard Disc Drive). Storage unit 140 stores a command received from server 200, and stores a parameter and the like set by a user.

Position detection unit 150 is included in, for example, a navigation device (not shown), and obtains absolute position information of vehicle 100 itself by using the GPS (Global Positioning System). Position detection unit 150 outputs the obtained position information to server 200.

Input unit 170 is formed by a touch panel, a switch or the like, and is included in, for example, the above-described navigation device. The user can set the parameter and the like by operating input unit 170.

Server 200 includes a control unit 210, a storage unit 220, a communication unit 230, and a display 240. Control unit 210 includes a pollution level determination unit 211, a map creation unit 212, a vehicle selection unit 213, and a command output unit 214.

Communication unit 230 is a communication interface between server 200 and communication network 300. Server 200 obtains vehicle information from vehicle 100 via communication unit 230, and outputs the movement command and the command to operate environment improvement device 120 to vehicle 100.

Storage unit 220 stores contents of the vehicle information received via communication unit 230. Storage unit 220 also prestores map information of a region where the environment improvement operation is to be executed.

Pollution level determination unit 211 included in control unit 210 calculates a pollution level for each predetermined area, using the concentration of the environmental pollutant included in the vehicle information transmitted from each vehicle 100, and determines necessity of the environment improvement operation. Map creation unit 212 associates the pollution level calculated by pollution level determination unit 211 with the map information stored in storage unit 220, and creates a pollution map. The created pollution map is displayed on display 240 such as a liquid crystal display panel, and thus, a server administrator and the like can visually recognize a state of environmental pollution.

For a target area determined as the environment improvement operation being necessary, vehicle selection unit 213 selects vehicles for executing the environment improvement operation in the target area, from vehicles 100 located in the target area or in an area close thereto. Command output unit 214 generates a command to execute the environment improvement operation, and outputs the command to selected vehicles 100.

Recently, environmental pollution by the particulate matter such as pollen or PM2.5 has been becoming serious. In order to reduce an influence of the particulate matter on health, it is necessary to prevent the generation of the particulate matter and quickly remove the generated particulate matter.

On the other hand, development of a device (environment improvement device) configured to remove the particulate matter is also proceeding, and a vehicle having the environment improvement device mounted thereon is also emerging.

Thus, in the present embodiment, there is proposed a system configured to improve a state of environmental pollution by using such a vehicle having an environment improvement device mounted thereon. More specifically, the present embodiment uses a method for detecting the state of pollution by the environmental pollutant for each area based on the information obtained from the sensor mounted on the vehicle or the fixed sensor, and moving the vehicles having the environment improvement devices mounted thereon to the area having a high pollution level, thereby removing the environmental pollutant. With such a configuration, the pollution level in the area can be reduced and the state of environmental pollution can be improved.

(Description of Contents of Control)

FIG. 3 shows one example of contents of the vehicle information transmitted from vehicle 100 to server 200. The vehicle information transmitted from each vehicle includes a vehicle ID for identifying the vehicle itself, a date of transmission, position information of the vehicle, the concentration of the environmental pollutant detected by sensor unit 110, a time period during which the environment improvement operation can be executed (available time period), and information about possibility of movement in accordance with the command from server 200 (movement possible information).

As to a coordinate indicated by the position information (X, Y, Z) of the vehicle in FIG. 3, X represents a longitude, Y represents a latitude, and Z represents an altitude, for example. Information about a travel direction (orientation) of the vehicle may be further included as the position information of the vehicle.

The available time period is a parameter that can be arbitrarily set by the user via input unit 170. The user sets a time period for which use of the vehicle is permitted for the environment improvement operation during a time period for which the vehicle is not used. Server 200 refers to the available time period and selects a vehicle used for the environment improvement operation. The environment improvement operation is executed within the available time period set by the user, which makes it possible to contribute to environment improvement while satisfying the user's needs.

The movement possible information is information indicating whether or not the vehicle can be moved to a specified area when the vehicle is used for the environment improvement operation. For example, when the target vehicle is placed in a home garage and a door of the garage is closed (locked), the vehicle cannot be moved from the garage to a specified location, although the environment improvement device can be used in the garage. Server 200 refers to the movement possible information and selects the target vehicle.

When server 200 obtains the vehicle information shown in FIG. 3 from vehicles 100, server 200 calculates the pollution level for each specified area on the map, using the position information of the vehicles and the information about the concentration of the environmental pollutant. For example, server 200 can use a maximum value of the concentrations of the environmental pollutant transmitted from vehicles 100 located in the same area, as the pollution level in the area. Alternatively, server 200 may use an average value of the concentrations of the environmental pollutant in the area as the pollution level.

Figure 4:
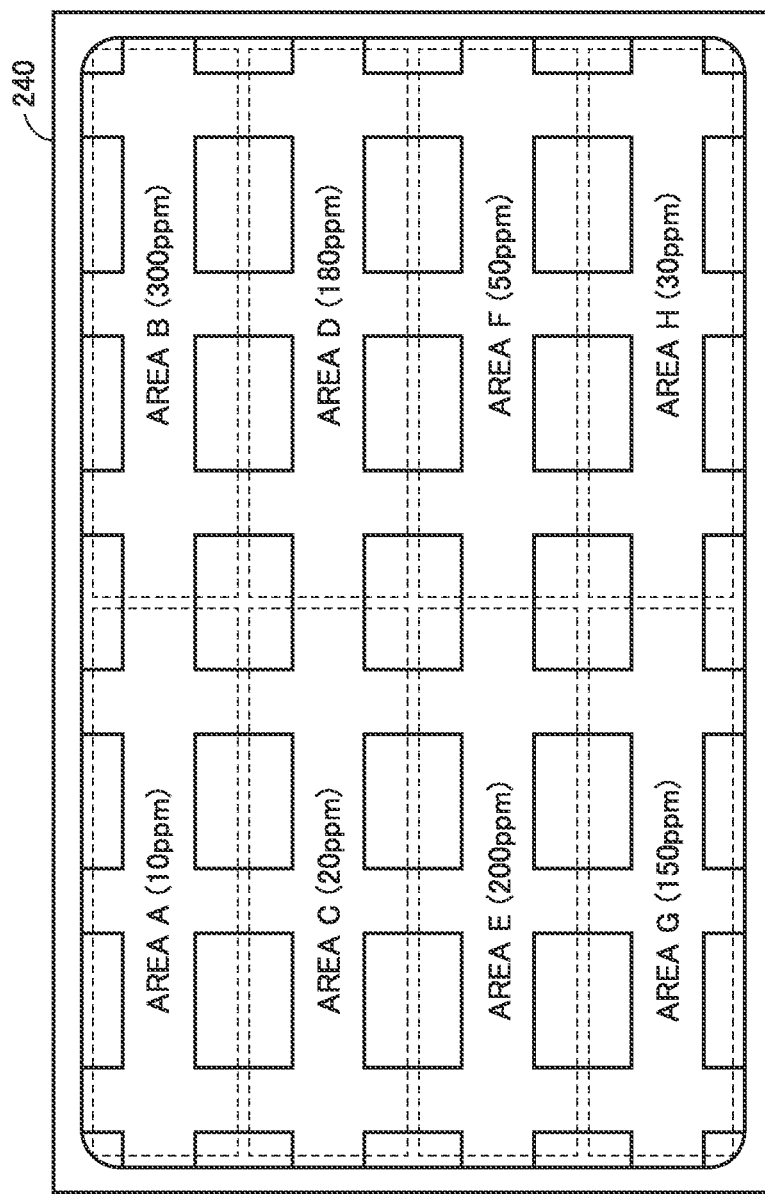
FIG. 4 shows one example of a map indicating a pollution level for each area created in the server.

Based on the calculated pollution level, server 200 creates a map of the pollution level shown in FIG. 4 and displays the map on display 240 of server 200. In the example in FIG. 4, a region displayed on display 240 is divided into eight rectangular areas, i.e., area A to area H, and the pollution level is displayed for each area. Area setting is not limited to the rectangular areas shown in FIG. 4, and may be, for example, administrative sections such as cities, or may be sections determined by main roads.

Based on whether or not the calculated pollution level exceeds a predetermined threshold value for each area, server 200 determines necessity of environment improvement in the area. FIG. 5 shows one example of determination of the necessity of environment improvement, and vehicle selection that are executed by server 200. In the example in FIG. 5, a threshold value of the pollution level for determining the necessity of environment improvement is, for example, 100 ppm, and it is determined that environment improvement is necessary in areas B, D, E, and G where their pollution levels exceed the threshold value. From vehicles 100 located in the region, server 200 selects vehicles executing the environment improvement operation in each area. Server 200 determines vehicles 100 to be selected, in consideration of the type of the environmental pollutant that should be removed and the type of the environmental pollutant that can be removed by the environment improvement device mounted on each vehicle 100. In addition, the available time period varies from vehicle 100 to vehicle 100, and thus, when a part of the initially selected vehicles becomes unavailable, server 200 further selects another vehicle located in the target area or in an area close thereto, instead of the unavailable vehicle.

When the area where environment improvement is executed and vehicles 100 used therefor are determined, server 200 generates a command shown in FIG. 6 and outputs the command to each vehicle 100. More specifically, server 200 transmits information about the area where environment improvement is executed, initial movement position information, and information about an operation manner in the area to each selected vehicle 100. The initial movement position information is information indicating a position where the vehicle is initially arranged. Each vehicle 100 moves to the position indicated by the initial movement position information from server 200 by automated driving, and then, executes the environment improvement operation based on the area information and the information about the operation manner.

When the operation manner is "stop", vehicle 100 moves to the initial movement position, and then, operates environment improvement device 120, with vehicle 100 being at a stop at that position. On the other hand, when the operation manner is "travel", vehicle 100 moves to the initial movement position, and then, travels autonomously in the specified area while operating environment improvement device 120. For example, in a location having a particularly high concentration of the environmental pollutant in the area, the environment improvement operation may be executed, with a particular vehicle being at a stop. The operation manner is preferably changed in accordance with the distribution of the state of pollution (concentration) by the environmental pollutant.

During execution of the environment improvement operation, each selected vehicle 100 transmits the vehicle information shown in FIG. 3 to server 200 at prescribed time intervals. Server 200 monitors a change in pollution level caused by execution of the environment improvement operation, and repeatedly executes the above-described operation. Then, when the pollution level in the specified area is improved and falls below the threshold value, server 200 outputs a command to stop environment improvement device 120 to each vehicle 100 that is executing the environment improvement operation in the area.

As described above, in the present embodiment, server 200 calculates the pollution level in each area based on the vehicle information from vehicles 100, and dispatches vehicles 100 having environment improvement devices 120 mounted thereon to the area having a high pollution level and causes vehicles 100 to execute the environment improvement operation. As a result, the environmental pollutant can be reduced by using vehicles 100 having environment improvement devices 120 mounted thereon.

Figure 7:
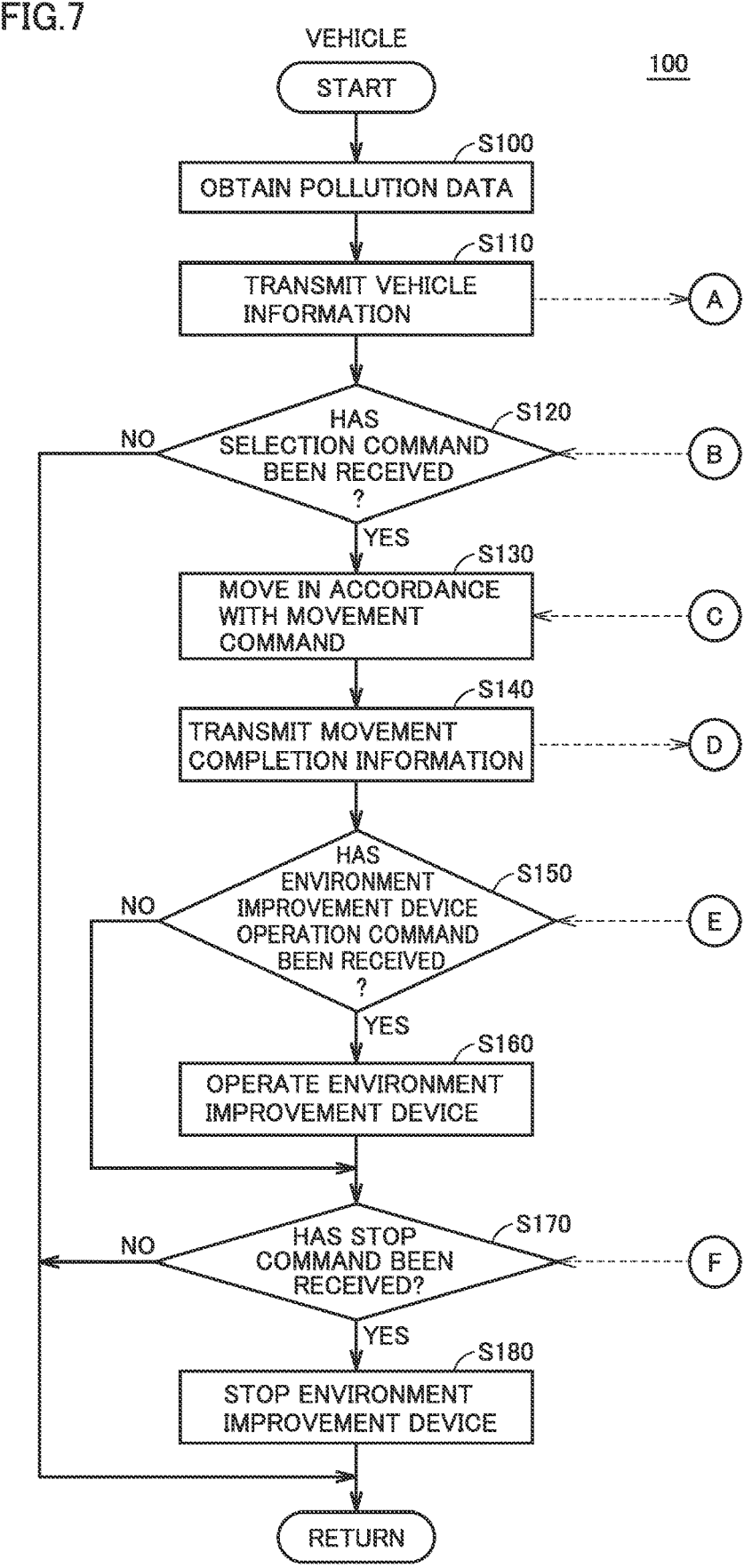
FIG. 7 is a flowchart for illustrating a detailed process of control executed in the vehicle.
Figure 8:
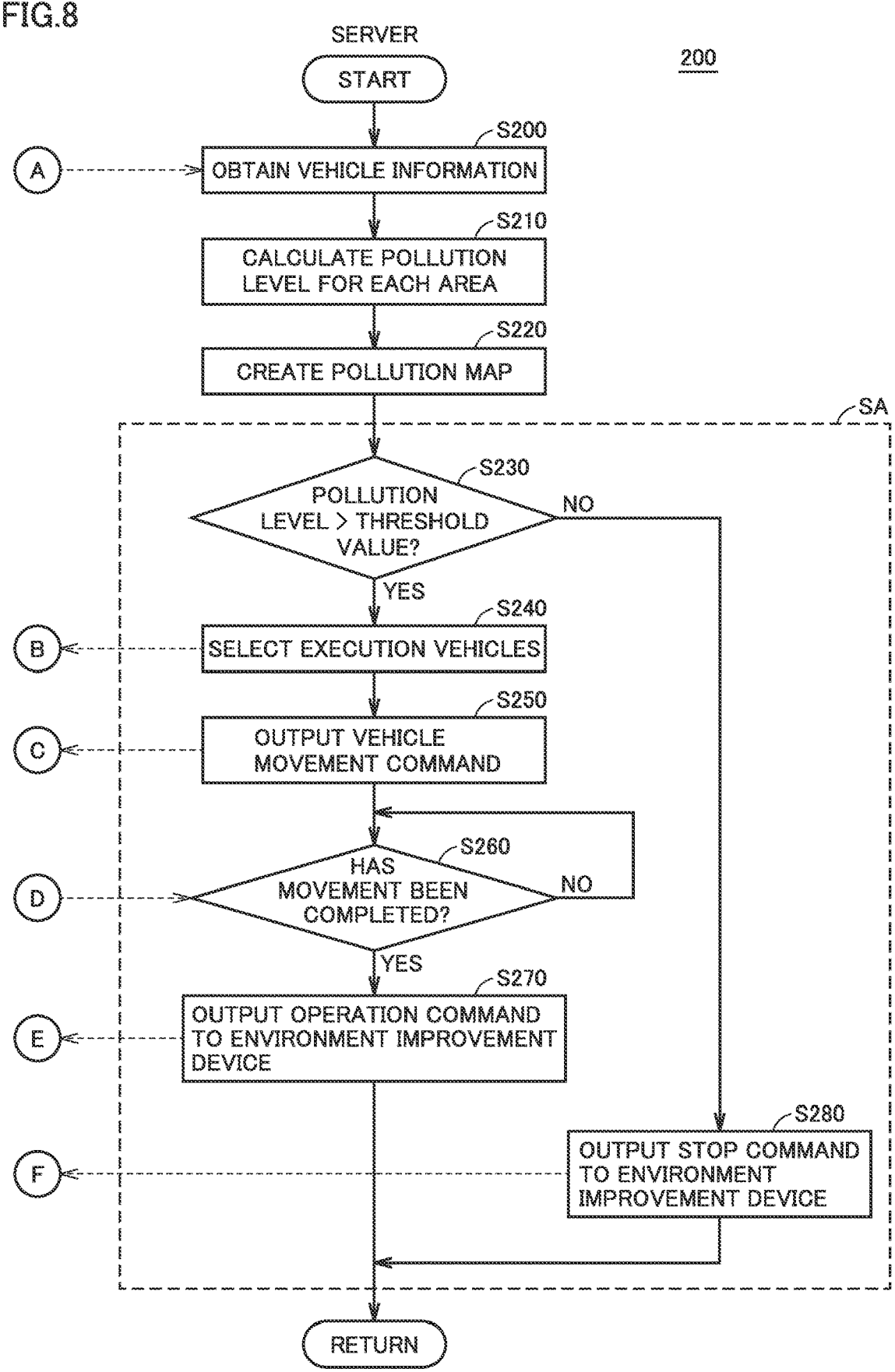
FIG. 8 is a flowchart for illustrating a detailed process of control executed in the server.

FIGS. 7 and 8 are flowcharts for illustrating details of control executed in vehicle 100 and server 200. The flowcharts shown in FIGS. 7 and 8 are implemented by invoking programs stored in controller 130 of vehicle 100 and control unit 210 of server 200 from a main routine and executing the programs when a prescribed cycle or a prescribed condition is satisfied. Alternatively, the processing in a part or all of the steps of the flowcharts can be implemented by dedicated hardware (electronic circuit).

Referring to FIG. 7, in step (hereinafter abbreviated as "S") 100, vehicle 100 obtains pollution data including the concentration of the environmental pollutant at the current position of vehicle 100, using sensor unit 110. Then, in S110, in addition to the pollution data obtained in S100, vehicle 100 transmits the vehicle information including the other information shown in FIG. 3 to server 200. When a plurality of types of environmental pollutants are detected, individual concentration data of each environmental pollutant may be included.

When vehicle 100 receives the command shown in FIG. 6 from server 200, vehicle 100 determines in S120 whether or not vehicle 100 itself has been selected as a target vehicle for executing the environment improvement operation. When vehicle 100 has not been selected as the target vehicle (NO in S120), vehicle 100 skips the following steps and returns the process to the main routine.

On the other hand, when vehicle 100 has been selected as the target vehicle (YES in S120), the process proceeds to S130 and vehicle 100 moves to the specified area by automated driving in accordance with the movement command transmitted from server 200. When vehicle 100 is, for example, a vehicle owned by a business operator specializing in environment improvement, automated driving is not necessarily required, and a driver of the business operator may drive vehicle 100 to the specified area in a manned manner in accordance with the command from server 200. Although not shown in FIG. 7, when vehicle 100 is selected as the target vehicle by server 200, vehicle 100 notifies the user that vehicle 100 has been selected as the target vehicle, using an email or the like.

When movement to the initial movement position specified by server 200 is completed, vehicle 100 transmits movement completion information to server 200 in S140. When vehicle 100 receives the command to operate environment improvement device 120 from server 200 in response (YES in S150), vehicle 100 operates environment improvement device 120, and maintains the state of being at a stop at the position or travels in the area in accordance with the specified operation manner (S160). When vehicle 100 does not receive the command to operate environment improvement device 120 from server 200 (NO in S150), vehicle 100 moves the process to S170, with environment improvement device 120 being at a stop.

In S170, vehicle 100 determines whether or not the command to stop environment improvement device 120 has been received from server 200. When the stop command has been received from server 200 with environment improvement device 120 being in operation (YES in S170), vehicle 100 stops environment improvement device 120 (S180) and returns the process to the main routine. On the other hand, when the stop command has not been received from server 200 with environment improvement device 120 being in operation (NO in S170), vehicle 100 maintains the operation of environment improvement device 120 and returns the process to the main routine. When environment improvement device 120 is still at a stop, the stop state of environment improvement device 120 is maintained regardless of reception of the stop command.

The foregoing description of S150 is about the initial state with environment improvement device 120 being at a stop. However, when the process in FIG. 7 is started with environment improvement device 120 being in operation, the operation of environment improvement device 120 is maintained regardless of whether determination in S150 is YES or NO.

Next, the process in server 200 will be described with reference to FIG. 8. When server 200 obtains the vehicle information from each vehicle 100 in S200, server 200 calculates the pollution level for each specified area, using the information about the concentration of the environmental pollutant included in the vehicle information from the vehicles located in the area (S210), and creates a pollution map of the entire region including the area (S220). The processing in S230 and the subsequent steps (processing in a broken line box SA in FIG. 8) is executed for each specified area.

In S230, server 200 determines whether or not the pollution level in the specified area exceeds the predetermined threshold value. When the pollution level is equal to or lower than the threshold value (NO in S230), server 200 determines that the environment improvement operation is unnecessary, and moves the process to S280. In S280, when each environment improvement device 120 is at a stop, the stop state is maintained. When each environment improvement device 120 is in operation, each environment improvement device 120 is stopped and the process is returned to the main routine.

On the other hand, when the pollution level is higher than the threshold value (YES in S230), server 200 determines that the environment improvement operation is necessary. Next, in S240, server 200 selects execution vehicles executing the environment improvement operation in the area, based on the position information of each vehicle 100, the information about the available time period and the like obtained as the vehicle information, and transmits the selection information to the vehicles in the area. In S250, server 200 outputs the movement command to selected vehicles 100. Transmission of the selection information of the execution vehicles and transmission of the movement command to vehicles 100 may be performed at different timings as shown in FIG. 8. Alternatively, however, the selection information and the movement command may be included in the same command and transmitted at the same timing.

Then, in S260, server 200 determines whether or not all of the vehicles selected for the specified area have moved to the respectively-set initial movement positions. When server 200 does not receive the movement completion information from each vehicle 100 (NO in S260), the process is returned to S260 and server 200 awaits for completion of movement of the execution vehicles.

On the other hand, when server 200 receives the movement completion information from each vehicle 100 and recognizes that movement of each vehicle to the set initial movement position has been completed (YES in S260), server 200 outputs the operation command to actuate environment improvement device 120 to each execution vehicle in S270, thereby causing each vehicle 100 to execute the environment improvement operation. Then, the process is returned to the main routine.

As described above, the processing in broken line box SA in FIG. 8 is executed for each area, and the environment improvement operation using vehicles 100 is continued until the pollution level in each area becomes equal to or lower than the prescribed threshold value. As a result, it is possible to reduce the environmental pollutant in the specified area and execute environment improvement using vehicles 100 including environment improvement devices 120.

The determination of the necessity of execution of the environment improvement operation in S230 above is not limited to determination by comparison between the pollution level and the prescribed threshold value in the foregoing description, and another determination method can also be used. For example, even if the pollution level does not exceed the threshold value, it may be determined that the environment improvement operation is necessary, when the pollution level is relatively higher than a pollution level in a surrounding area (when a difference between the pollution level in the specified area and the pollution level in the surrounding area is equal to or larger than a prescribed value). Alternatively, it may be determined that the environment improvement operation is necessary, when the pollution level is expected to increase in the future based on a change in pollution level over time (when a time change rate of the pollution level is equal to or higher than a prescribed value).

Vehicle 100 used in environment improvement system 10 described above may be a general vehicle for household use, or may be a dedicated vehicle developed to remove an environmental pollutant.

When a privately-owned vehicle is used as vehicle 100, privileges such as a discount or a refund of a fee for charging an electrically-powered vehicle may, for example, be provided depending on the utilization time. Alternatively, free replacement of consumables such as a filter of the environment improvement device or prioritized upgrade to a device having a more excellent environment improvement effect may be provided to a vehicle that greatly contributes to the environment improvement operation. By providing such privileges, an incentive for participation and cooperation in the environment improvement operation can be given to the user of each vehicle, and thus, environment improvement can be promoted.

Vehicle 100 including both sensor unit 110 and environment improvement device 120 may operate environment improvement device 120 and execute the environment improvement operation regardless of whether or not the command is received from server 200, when it is determined that removal of the environmental pollutant is necessary, based on the state of pollution detected by sensor unit 110.

(First Modification)

In the foregoing description of the embodiment, the case of each vehicle including both the sensor unit and the environment improvement device has been described. However, each vehicle does not necessarily need to include both the sensor unit and the environment improvement device. A vehicle including only the sensor unit, a vehicle including only the environment improvement device, and a vehicle including both the sensor unit and the environment improvement device may be mixed. In this case, the server determines the necessity of execution of the environment improvement operation, based on information from the vehicles having the sensor units mounted thereon (the vehicle including only the sensor unit and the vehicle including both the sensor unit and the environment improvement device), and executes the environment improvement operation by using the vehicles having the environment improvement devices mounted thereon (the vehicle including only the environment improvement device and the vehicle including both the sensor unit and the environment improvement device).

(Second Modification)

In the foregoing description, the case of using a vehicle as the movable body has been described. However, the movable body may include not only a vehicle but also a person. For example, the sensor unit mounted on the movable body in the foregoing description may be mounted on a mobile terminal (such as a smartphone), or a wearable sensor and the like that can be worn on a body can also be used. As the environment improvement device, a portable-type device that can be conveyed by a person can also be used.

While the embodiment of the present disclosure has been described, it should be understood that the embodiment disclosed herein is illustrative and non-restrictive in every respect. The scope of the present disclosure is defined by the terms of the claims and is intended to include any modifications within the scope and meaning equivalent to the terms of the claims.

What is claimed is:

1. An environment improvement system comprising:
a sensor configured to detect a state of pollution by an environmental pollutant;
a plurality of ground-based outdoor movable bodies; and
a server configured to communicate with the plurality of ground-based outdoor movable bodies,
the plurality of ground-based outdoor movable bodies comprising ground-based outdoor movable bodies including environment improvement devices configured to remove the environmental pollutant,
when the state of pollution detected by the sensor enters a state in which removal of the environmental pollutant is necessary in an area where the sensor is located, the server being configured to (i) select at least a part of the ground-based outdoor movable bodies including the environment improvement devices and cause the selected ground-based outdoor movable bodies to move to the area, and (ii) output a command to execute an environment improvement operation using the environment improvement devices, wherein
the movable bodies including the environment improvement devices configured to send to the server an available time period thereof that is preset by a user, and
the server is further configured to select at least a part of the movable bodies to execute the environment improvement operation based on the available time period sent by each of the movable bodies.

2. The environment improvement system according to claim 1, wherein the plurality of ground-based outdoor movable bodies comprise a ground-based outdoor movable body including the sensor.

3. The environment improvement system according to claim 2, wherein the server is configured to calculate a pollution level for each predetermined area, using position information of the ground-based outdoor movable body including the sensor and information about the state of pollution, and determine necessity of removal of the environmental pollutant, using the pollution level.

4. The environment improvement system according to claim 1, wherein the server is configured to select a ground-based outdoor movable body including an environment improvement device corresponding to a type of the environmental pollutant, of the ground-based outdoor movable bodies including the environment improvement devices.

5. The environment improvement system according to claim 1, wherein at least a part of the selected ground-based outdoor movable bodies execute the environment improvement operation while moving in a specified area.

6. The environment improvement system according to claim 1, wherein a ground-based outdoor movable body including both the sensor and the environment improvement device, of the plurality of ground-based outdoor movable bodies, executes the environment improvement operation regardless of reception of the command from the server, when the state of pollution detected by the sensor provided in the ground-based outdoor movable body enters the state in which removal of the environmental pollutant is necessary.

7. The environment improvement system according to claim 1, wherein the command includes information about an operation manner in the area, the operation manner being at least one of a stop operation manner and a travel operation manner, the stop operation manner being a manner in which the selected ground-based outdoor movable bodies are at a stop in the area while the environment improvement operation is being performed, and the operation manner being changed in accordance with a distribution of the state of pollution by the environment pollutant.

8. A server used in a system configured to improve a state of pollution by an environmental pollutant by using ground-based outdoor movable bodies having environment improvement devices mounted thereon,
the server being configured to communicate with a plurality of ground-based outdoor movable bodies,
the plurality of ground-based outdoor movable bodies comprising the ground-based outdoor movable bodies having the environment improvement devices mounted thereon, wherein the ground-based outdoor movable bodies are configured to send to the server an available time period thereof that is preset by a user,
the server being configured to:
obtain information about the state of pollution by the environmental pollutant from a sensor;
using the information from the sensor, determine whether or not the state of pollution in an area where the sensor is located is a state in which removal of the environmental pollutant is necessary;
when it is determined that removal of the environmental pollutant in the area is necessary, select at least a part of the ground-based outdoor movable bodies having the environment improvement devices mounted thereon; and
cause the selected ground-based outdoor movable bodies to move to the area and execute an environment improvement operation using the environment improvement devices in the area, wherein
the step of causing comprises outputting a command to execute the environment improvement operation,
the server is further configured to
obtain from the ground-based outdoor movable bodies the available time period thereof that is preset by the user, and
select at least a part of the ground-based outdoor movable bodies to execute the environment improvement operation based on the available time period sent by each of the ground-based outdoor movable bodies.

9. The server according to claim 8, wherein the command includes information about an operation manner in the area, the operation manner being at least one of a stop operation manner and a travel operation manner, the stop operation manner being a manner in which the selected ground-based outdoor movable bodies are at a stop in the area while the environment improvement operation is being performed, and the operation manner being changed in accordance with a distribution of the state of pollution by the environment pollutant.

10. An environment improvement method for improving an environment of an area where a sensor is located by using environment improvement devices mounted on ground-based outdoor movable bodies in a system, based on a state of pollution by an environmental pollutant detected by the sensor, the system including a plurality of ground-based outdoor movable bodies and a server configured to communicate with the plurality of ground-based outdoor movable bodies,
the plurality of ground-based outdoor movable bodies comprising the ground-based outdoor movable bodies having the environment improvement devices mounted thereon,
the movable bodies including the environment improvement devices are configured to send to the server an available time period thereof can be preset by a user,
the environment improvement method comprising, by the server:
determining whether or not the state of pollution in the area is a state in which removal of the environmental pollutant is necessary;
when it is determined that removal of the environmental pollutant in the area is necessary, selecting at least a part of the ground-based outdoor movable bodies having the environment improvement devices mounted thereon;
causing the selected ground-based outdoor movable bodies to move to the area; and
causing the selected ground-based outdoor movable bodies to execute an environment improvement operation using the environment improvement devices in the area, wherein
the step of selecting at least a part of the movable bodies includes:
obtaining from the movable bodies the available time period thereof that is preset by the user, and
selecting at least a part of the movable bodies to execute the environment improvement operation based on the available time period sent by each of the movable bodies.

11. The environment improvement method according to claim 10, wherein the command includes information about an operation manner in the area, the operation manner being at least one of a stop operation manner and a travel operation manner, the stop operation manner being a manner in which the selected ground-based outdoor movable bodies are at a stop in the area while the environment improvement operation is being performed, and the operation manner being changed in accordance with a distribution of the state of pollution by the environment pollutant.

* * * * *